United States Patent [19]

Ohki et al.

[11] Patent Number: 4,464,361

[45] Date of Patent: Aug. 7, 1984

[54] ADENOSINE DERIVATIVES

[75] Inventors: Sadao Ohki; Fumiko Hamaguchi, both of Tokyo; Tatsuo Nagasaka; Hiroyuki Kikuchi, both of Hachiohji, all of Japan

[73] Assignee: Fujisawa Pharmaceutical Co., Ltd., Osaka, Japan

[21] Appl. No.: 368,416

[22] Filed: Apr. 14, 1982

[30] Foreign Application Priority Data

Apr. 15, 1981 [JP] Japan ............................... 56-57466

[51] Int. Cl.³ ..................... A61K 31/70; C07H 19/06
[52] U.S. Cl. ..................................... 424/180; 536/26
[58] Field of Search ........................... 536/26; 424/180

[56] References Cited

U.S. PATENT DOCUMENTS 3,590,029 6/1971 Koch et al. ............................ 536/26
3,901,876 8/1975 Vorbrüggen et al. ................. 536/26
3,988,317 10/1976 Kampe et al. ......................... 536/26

FOREIGN PATENT DOCUMENTS 2139107 2/1973 Fed. Rep. of Germany .
2406587 8/1975 Fed. Rep. of Germany .
   8412 3/1971 France .

OTHER PUBLICATIONS

Kawazoe et al., Arzneim-Forsch./Drug Res. 30 (II), p. 1083 (1980).
Takeshi Endo et al., "Oxidation of N6, N6-Dialkyl-2', 3', 5'-tri-O-acyl adenosines with ruthenium tetroxide and a novel selective N-monodealkylation sequence," Journal of Organic Chemistry, vol. 44, No. 21 (1979) pp. 3652-3656.
Y. Midorikawa et al., "Conversion of Hypoxanthine Derivatives to Succinyladenine Derivatives by Bacillus subtilis," Chemical Abstracts, vol. 77, No. 25 (1972) p. 285, Abstract No. 163025r.

Primary Examiner—Ethel G. Love
Attorney, Agent, or Firm—Oblon, Fisher, Spivak, McClelland & Maier

[57] ABSTRACT

Adenosine derivatives of the general formula:

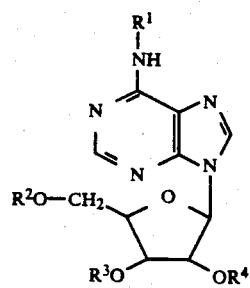

wherein $R^1$ is a group of the formula:

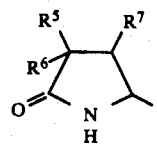

in which $R^5$ and $R^6$ are each hydrogen, alkoxy or arylthio and $R^7$ is hydrogen or halogen, or a group of the formula:

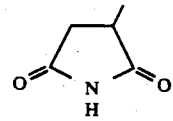

and $R^2$, $R^3$ and $R^4$ are each hydrogen or alkanoyl, and pharmaceutically acceptable salt thereof.

These derivatives and salts thereof are useful as antihypertensives, bradycardiacs, etc. The method of production thereof and pharmaceutical compositions based on those adenosine derivatives or salts are also described.

4 Claims, No Drawings

ADENOSINE DERIVATIVES

This invention relates to novel adenosine derivatives and salts thereof. More particularly, this invention relates to a novel adenosine derivative, inclusive of a salt thereof, which has antihypertensive, cardiovascular and bradycardic activities, to processes for preparing said derivative or salt, and to a pharmaceutical composition containing the same.

The adenosine derivative according to this invention may be represented by the following general formula (I)

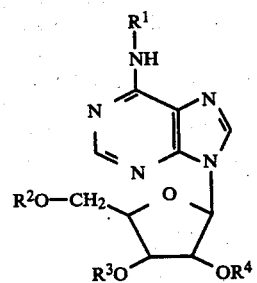

wherein
$R^1$ is a group of the formula:

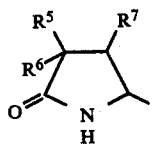

in which $R^5$ and $R^6$ are each hydrogen, alkoxy or arylthio and $R^7$ is hydrogen or halogen, or a group of the formula

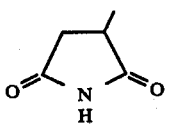

and $R^2$, $R^3$ and $R^4$ are each hydrogen or alkanoyl, and pharmaceutically acceptable salt thereof.

The pharmaceutically acceptable salt of adenosine derivatives (I) of the invention includes acid addition salts such as the corresponding hydrochloride, sulfate, nitrate, etc.

Some of the various terms used throughout this specification and the claims appended thereto have the following defined meanings.

First, the term "lower" refers to a group containing 1 to 6 carbon atoms unless otherwise indicated.

The "alkanoyl" for $R^2$, $R^3$ and $R^4$ means the residues of aliphatic carboxylic acids and, as suitable examples thereof, lower alkanoyl groups such as formyl, acetyl, propionyl, butyryl, etc.

The "alkoxy" for $R^5$ and $R^6$ includes lower alkoxy groups such as methoxy, ethoxy, propoxy, isopropoxy, butoxy, isobutoxy, t-butoxy, pentyloxy, hexyloxy, etc.

The "arylthio" for $R^5$ and $R^6$ includes, for example, phenylthio, tolylthio, xylylthio, naphthylthio, etc.

The "halogen" for $R^7$ means chloro, bromo, fluoro or iodo.

The adenosine derivative (I) according to this invention can be produced by the following and other alternative processes.

Process 1      (1)

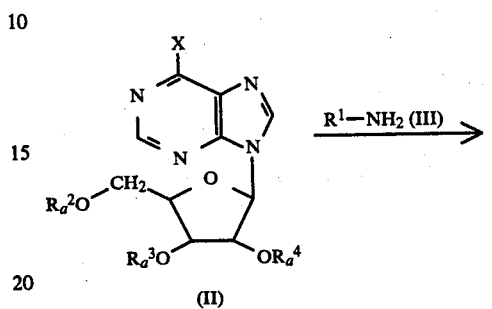

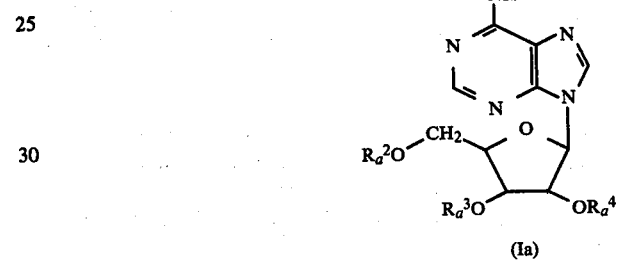

Process 2      (2)

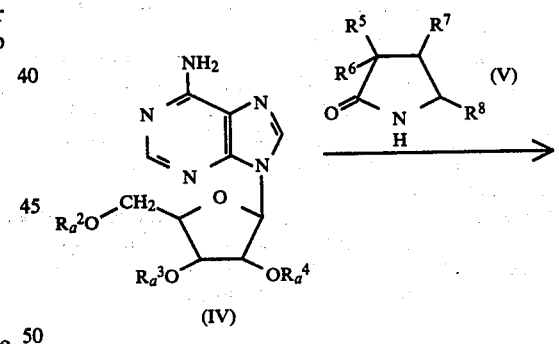

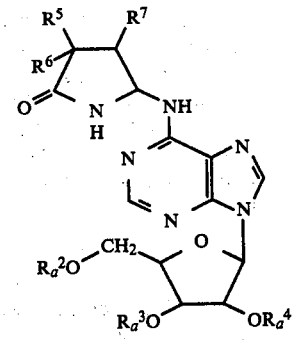

Process 3      (3)

-continued

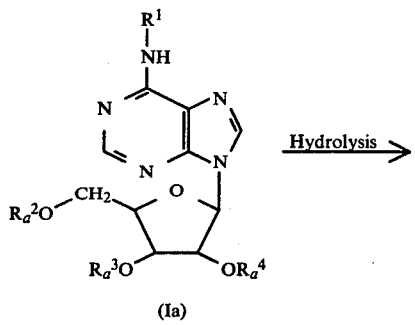

(Ia)

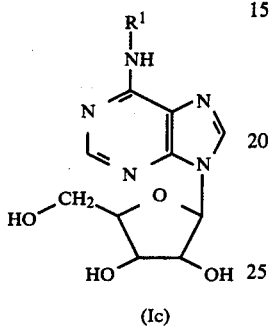

(Ic)

($R^1$, $R^5$, $R^6$ and $R^7$ have the same meanings as defined hereinbefore, $R_a^2$, $R_a^3$ and $R_a^4$ are each alkanoyl, $R^8$ is alkoxy, and X is halogen).

The above processes 1 through 3 are described in detail.

PROCESS 1

The compound (Ia) or its salt can be produced by reacting a compound (II) with a compound (III) or a salt thereof.

Of the compounds (II), 6-chloro-9-β-D-ribofuranosylpurine 2',3',5'-triacetate, for instance, can be produced for example by the process described in Journal of Organic Chemistry 28, 945 (1963), and the other compounds (II) can also be produced by processes analogous thereto.

Of the compounds (III), 5-amino-2-pyrrolidinone, for instance, can be produced for example by the process described in Heterocycles 14, 1245 (1980) and the other compounds (III) can also be produced by processes analogous thereto.

As salts of compound (III), there may be mentioned acid addition salts such as the corresponding hydrochloride, sulfate and nitrate.

This reaction is generally carried out in a solvent and in many cases at room temperature or under heating.

As examples of such reaction solvent may be mentioned methanol, ethanol, propanol, etc. and, for that matter, any solvent that will not interfere with the reaction.

PROCESS 2

The compound (Ib) or a salt thereof can be produced by reacting a compound (IV) or a salt thereof with a compound (V).

Of the compounds (V), 5-ethoxy-2-pyrrolidinone, for instance, can be produced by the process described in Tetrahedron 31, 1437 (1975) and the other compounds (V) can also be produced by processes analogous thereto.

As examples of salts of (V), there may be mentioned acid addition salts such as the corresponding hydrochloride, sulfate and nitrate.

This reaction is often carried out in a solvent that will not interfere therewith either at room temperature or under heating.

PROCESS 3

The compound (Ic) or a salt thereof can be produced by hydrolyzing a compound (Ia) or a salt thereof.

This hydrolysis reaction is generally conducted in a solvent such as methanol, ethanol, propanol, etc. and in many cases in the presence of a base such as ammonia, an alkoxide (e.g. sodium methoxide, potassium ethoxide, magnesium methoxide, etc.) or the like.

Moreover, this reaction is in many cases conducted under cooling or in the neighborhood of room temperature.

The product compounds (Ia), (Ib) and (Ic) in the above processes 1 to 3 can be isolated and purified from the respective reaction mixtures by procedures known per se.

The pharmacological activities of the adenosine derivatives and salts according to this invention will now be described by way of the following Test.

(a) Test compounds

| Test compound No. | $R^1$ | $R^2$ | $R^3$ | $R^4$ |
|---|---|---|---|---|
| 1 | | CH₃CO— | CH₃CO— | CH₃CO— |
| 2 | | CH₃CO— | CH₃CO— | CH₃CO— |
| 3 | ![pyrrolidinone] | H | H | H |
| 4 | | H | H | H |

-continued

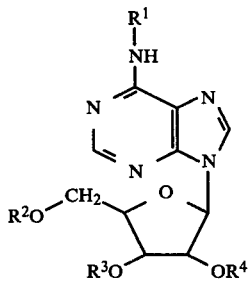

| Test compound No. | R¹ | R² | R³ | R⁴ |
|---|---|---|---|---|
| 5 | 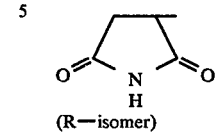 (R—isomer) | H | H | H |
| 6 | 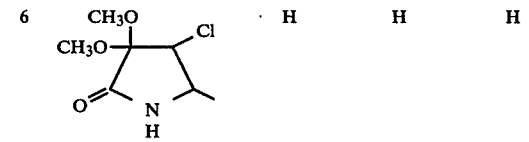 | H | H | H |
| 7 | 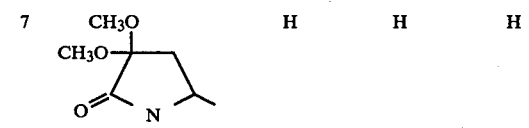 | H | H | H |
| 8 | 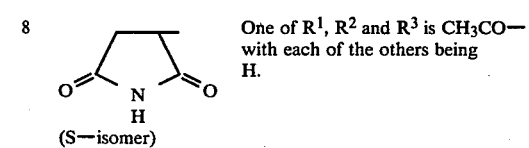 (S—isomer) | One of R¹, R² and R³ is CH₃CO— with each of the others being H. | | |
| 9 | 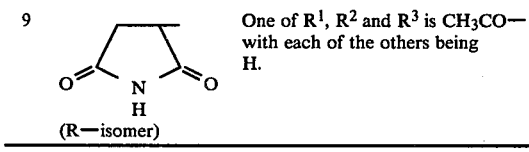 (R—isomer) | One of R¹, R² and R³ is CH₃CO— with each of the others being H. | | |

(b) Test method

Male spontaneously hypertensive rats (SHR) each weighing about 300 grams, in groups of 4 individuals, were first anesthetized with pentobarbital (50 mg/kg, intraperitoneal injection) and then dosed intravenously with the test compounds. The femoral artery blood pressure of each rat was measured and, at the same time, its heart rate was estimated from the blood pressure pulse waves. The following table shows the results in terms of percent average blood pressure falls and percent average heart rate decreases after administration of the respective compounds.

(c) Results

| Test compound No. | Dosage (μg/kg) | Antihypertensive activity (% blood pressure fall) | Bradycardiac activity (% heart rate decrease) |
|---|---|---|---|
| 1 | 100 | 2 | 16 |
|  | 300 | 15 | 48 |
|  | 1000 | 35 | 62 |
| 2 | 10 | 6 | 32 |
|  | 30 | 42 | 58 |
| 3 | 30 | 21 | 19 |
|  | 100 | 50 | 45 |
| 4 | 30 | 10 | 41 |
|  | 100 | 55 | 66 |
| 5 | 3 | 4 | 39 |
|  | 30 | 64 | 66 |
| 6 | 300 | 48 | 15 |
| 7 | 1000 | 13 | 7 |
| 8 | 100 | 12 | 29 |
| 9 | 10 | 14 | 43 |
|  | 30 | 41 | 46 |

The adenosine derivatives (I) and their pharmaceutically acceptable salts which have antihypertensive, cardiovascular and bradycardic activities and are useful as antihypertensive agents and cardiovascular agents, bradycardic agents. The adenosine derivatives (I) and their pharmaceutically acceptable salts can be orally or parenterally administered to mammalian animals including man in such dosage forms as capsules, tablets, suspensions, solutions and so forth. Such preparations can be manufactured with the use of suitable carriers or vehicles such as diluents, extenders, granulation aids, preservatives, binders, flavoring agents, coating materials, etc. The dosage of said adenosine derivatives (I) and salts depend on such factors as body weight, age, route of administration, etc. Usually, however, the dose level is generally selected from the range of 10 to 1000 mg/day as the active compound, although deviations from the range are permissible when considered necessary from clinical points of view.

The following examples are given to illustrate this invention in further detail.

EXAMPLE 1

6-Chloro-9-β-D-ribofuranosylpurine 2′,3′,5′-triacetate (4.1 g) and 5-amino-2-pyrrolidinone (3.0 g) were heated in ethanol (100 ml) under reflux for 10 hours, after which the solvent was distilled off. The residue was extracted with chloroform and the extract was washed with water, dried and concentrated under reduced pressure. The residue was chromatographed on a silica gel column and elution was carried out with chloroform-acetone (5:3). The active fractions were pooled and concentrated under reduced pressure to give N⁶-(5-oxo-2-pyrrolidinyl)adenosine 2′,3′,5′-triacetate as an oil (2.4 g).

NMR (CDCl₃, characteristic peak): δppm; 2.1 (6H,s, COCH₃×2), 2.13 (3H,s,COCH₃)

EXAMPLE 2

Adenosine 2′,3′,5′-triacetate (2.0 g) and 5-ethoxy-2-pyrrolidinone (1.2 g) were stirred in N,N-dimethylformamide (10 ml) at 130° C. overnight. The reaction mixture was distilled to remove the N,N-dimethylformamide and the residue was subjected to silica gel column chromatography using chloroformacetone (5:3) as the eluent. The active fractions were pooled and concentrated under reduced pressure to give N⁶-(5-oxo-2-pyrrolidinyl)adenosine 2′,3′,5′-triacetate as an oil (2.2 g).

NMR (CDCl₃, characteristic peak): δppm; 2.1 (6H,s, COCH₃×2), 2.13 (3H,s,COCH₃)

EXAMPLE 3

(1) 5-Ethoxy-2-pyrrolidinone (1.3 g) and an excess of hexamethyldisilazane (10 g) were heated under reflux for 4 hours, at the end of which time the mixture was concentrated under reduced pressure. The oily residue was then distilled under reduced pressure to give 1-trimethylsilyl-5-ethoxy-2-pyrrolidinone as an oil (1.9 g).

b.p., 2 mmHg: 68°–69° C.

IR (neat): $\nu$max=1685, 1070 cm$^{-1}$

NMR (CDCl$_3$): $\delta$ppm; 0.30 (9H,s); 1.23 (3H,t,J=7 Hz); 1.9–2.4 (4H, m); 3.43 (2H, m); 4.93 (1H,m)

(2) A solution of lithium diisopropylamide (1.54 g) in dry tetrahydrofuran (20 ml) was prepared (using 20 mmoles of diisopropylamine and 14.4 mmoles of n-butyl lithium), and at −78° C., a solution of 1-trimethylsilyl-5-ethoxy-2-pyrrolidinone (1.2 g) in tetrahydrofuran (3 ml) was added dropwise over a period of 10 minutes. Thereafter, the reaction mixture was stirred at −78° C. for 2 hours, at the end of which a solution of diphenyl disulfide (2.62 g) in tetrahydrofuran (6 ml) was added dropwise over a period of 10 minutes. The mixture was stirred at −78° C. for an additional hour, and then, warmed to room temperature gradually over a period of 2 hours. The reaction mixture was diluted with water (20 ml) and stirred at room temperature for 20 minutes. The reaction mixture was then extracted with ether and the extract was washed with a 5% aqueous solution of sodium hydroxide and a saturated aqueous solution of sodium chloride in the order mentioned. It was then dried over magnesium sulfate and the ether was distilled off under reduced pressure. The resulting yellow oil (2.32 g) was subjected to silica gel column chromatography using chloroform as the eluent. The active fractions were pooled and concentrated to give crude crystals, which were further recrystallized from isopropyl alcohol to give 3,3-diphenylthio-5-ethoxy-2-pyrrolidinone as colorless needles (1.73 g).

m.p.: 92°–93° C.

Elemental analysis (%): Calcd. (C$_{18}$H$_{19}$NO$_2$S$_2$): C, 62.58; H, 5.54; N, 4.05; Found: C, 62.58; H, 5.55; N, 3.97 C$_2$H$_5$OH UV: $\lambda_{max}^{C_2H_5OH}$: 202, 220, 264 nm IR (KBr): $\nu$max: 3180, 1690, 1100 cm$^{-1}$ NMR (CDCl$_3$): $\delta$ppm; 1.07 (3H,t,J=7 Hz); 2.37 (2H,m); 3.30 (2H,m); 4.47 (1H,d-d,J=6 Hz, J=3 Hz); 7.2–7.8 (10H,m); 8.13 (1H,broad)

(3) Adenosine 2′,3′,5′-triacetate (110 mg) and 3,3-diphenylthio-5-ethoxy-2-pyrrolidinone (155 mg) were heated in toluene (10 ml) under reflux for 5 hours, at the end of which the reaction solvent was distilled off under reduced pressure. The residue was subjected to silica gel column chromatography using chloroform-acetone (5:1) as the eluent. The active fractions were pooled and concentrated under reduced pressure to give crystals which were recrystallized from ethanol. By the above procedure was obtained N$^6$-(3,3-diphenylthio-5-oxo-2-pyrrolidinyl)adenosine 2′,3′,5′-triacetate as colorless needles (108 mg).

m.p.: 178°–179° C.

Mass spectrum: m/e=394, 259, 190, 136, 109

IR (KBr): $\nu$max=3150, 1740, 1720, 1610 cm$^{-1}$

NMR (CDCl$_3$): $\delta$ppm; 2.04 (3H,s); 2.10 (3H,s); 2.14 (3H,s); 2.8 (2H,m); 4.36 (2H,s); 5.12 (1H,s); 7.2–7.8 (10H,m); 7.86 (1H,s); 8.28 (1H,s)

EXAMPLE 4

6-Chloro-9-$\beta$-D-ribofuranosylpurine 2′,3′,5′-triacetate (500 mg) and L-3-aminosuccinimide (570 mg) were heated in dry tetrahydrofuran (30 ml) under reflux for 38 hours. The tetrahydrofuran was distilled off under reduced pressure and the residue was extracted with chloroform. The extract was washed with water and dried over magnesium sulfate. The chloroform was then distilled off under reduced pressure to give an oil (600 mg). This oil was further subjected to silica gel column chromatography using chloroform-ethanol (9:1) as the eluent. The active fractions were pooled and concentrated under reduced pressure and the residual crystals were recrystallized from chloroform to give N$^6$-[(S)-2,5-dioxo-3-pyrrolidinyl] adenosine 2′,3′,5′-triacetate as colorless needles (460 mg).

m.p.: 159°–160° C.

Elemental analysis (%): Calcd. (C$_{20}$H$_{22}$N$_6$O$_9$·H$_2$O): C, 47.24; H, 4.76; N, 16.53 Found: C, 47.12; H, 4.68; N, 16.16

IR (KBr): $\mu$max=3300, 1745, 1720, 1615, 1230 cm$^{-1}$

Mass spectrum: m/e=490 (M$^+$)

NMR (CDCl$_3$): $\delta$ppm; 2.06 (3H,s); 2.13 (6H,s); 3.0 (2H,m); 4.40 (2H,s); 5.10 (1H,m); 5.70 (1H,m); 5.96 (1H,t,J=5 Hz); 6.20 (1H,d,J=5 Hz); 7.70 (1H,m); 8.07 (1H,s); 8.33 (1H,s); 10.66 (1H,m)

EXAMPLE 5

The following compound was obtained in the similar manner as Example 4.

N$^6$-[(R)-2,5-dioxo-3-pyrrolidinyl]adenosine 2′,3′,5′-triacetate

IR (KBr): $\mu$max; 1745, 1725, 1615 cm$^{-1}$

NMR (DMSO-d$_6$): $\delta$ppm; 2.02 (6H,s); 2.10 (3H,s); 2.84 (2H,t,J=9 Hz), 4.16 (3H,m); 5.00 (1H,broad); 5.56 (1H,t,J=5 Hz); 6.00 (1H,t,J=5 Hz); 6.20 (1H,d,J=5 Hz); 8.19 (1H,s); 8.38 (1H,broad s); 8.38 (1H,s)

EXAMPLE 6

To N$^6$-(5-oxo-2-pyrrolidinyl)adenosine 2′,3′,5′-triacetate (2.2 g) was added cold ammonia-saturated methanol (40 ml), and the resulting mixture was allowed to stand in a refrigerator (at 4° C.) overnight. Next morning the solvent was removed at room temperature. To the residue was added a small amount of methanol and the mixture was allowed to stand at room temperature. The resulting precipitate was recovered by filtration and dried to give N$^6$-(5-oxo-2-pyrrolidinyl)adenosine as crystals (1.098 g).

m.p.: 198°–200° C.

IR (KBr): $\nu$max; 3220, 1680, 1610 cm$^{-1}$

Elemental analysis (%): Calcd. (C$_{14}$H$_{18}$N$_6$O$_5$): C, 47.99; H, 5.18; N, 23.99; Found: C, 47.45; H, 5.37; N, 24.10

EXAMPLE 7

(1) In methanol (50 ml) was dissolved sodium metal (1.5 g), followed by cooling to −10° C. Then, 3-chloro-5-hydroxy-2(5H)-furanone (2.69 g) was gradually added to the above solution and the mixture was allowed to stand at 5° C. for about 2 hours. To this reaction mixture was added 500 ml of benzene, followed by addition of HCl-saturated methanol (9 ml). The mixture was immediately distilled under reduced pressure and the residue was extracted with benzene. The extract was concentrated under reduced pressure and the residual oil was subjected to silica gel column chromatography using hexane-acetone (20:1) as the eluent. The active fractions were pooled and concentrated under reduced pressure to give crystals. Recrystallization from hexane yielded 3,4-dihydro-3,3,5-trimethoxy-2(5H)-furanone as crystals (1.47 g).

m.p.: 55° C.

(2) Concentrated aqueous ammonia (3 ml) was cooled to −10° C. and 3,4-dihydro-3,3,5-trimethoxy-2(5H)-furanone (1 g), obtained above in (1), was gradually added. The mixture was stirred at room temperature for about 15 minutes. This reaction mixture was concentrated under reduced pressure and the oily residue was dissolved in methanol (50 ml), followed by addition of p-toluenesulfonic acid (150 mg). The mixture was refluxed for about 1 hour, at the end of which it was concentrated under reduced pressure. The residue was subjected to silica gel column chromatography using hexane-acetone (5:1) as the eluent. The active fractions were pooled and concentrated under reduced pressure to give crystals. Recrystallization from hexane gave 3,3,5-trimethoxy-2-pyrrolidinone as crystals (700 mg).

m.p.: 86° C.

(3) 3,3,5-Trimethoxy-2-pyrrolidinone (445 mg) was evenly admixed with adenosine 2′,3′,5′-triacetate (1 g) and the mixture was melted and reacted by heating at 160° C. for 2 hours. The reaction mixture was then allowed to cool and subjected to silica gel column chromatography using benzene-acetone (2:1) as the eluent to give $N^6$-(3,3-dimethoxy-2-oxo-5-pyrrolidinyl)adenosine 2′,3′,5′-triacetate (1 g). This product was dissolved in ammonia-saturated methanol (30 ml) and left standing at 5° C. for 17 hours, after which time it was concentrated under reduced pressure. The residue was washed with benzene and the insolubles were subjected to silica gel column chromatography using chloroform-methanol (10:1) as the eluent. The active fractions were pooled and concentrated under reduced pressure to give crystals. Recrystallization from methanol-acetone yielded $N^6$-(3,3-dimethoxy-2-oxo-5-pyrrolidinyl)adenosine as colorless crystals (680 mg).

m.p.: 176°–178° C.

u.v.: $\lambda_{max}^{C_2H_5OH}$: 265 nm

IR (KBr): $\nu$: 3500–3000 (broad), 2970, 2920, 2820, 1700, 1615 cm$^{-1}$

NMR (DMSO-d$_6$); δppm: 2.36 (1H,dd,J=6 Hz,14 Hz); 2.55 (1H,dd,J=6 Hz,14 Hz); 3.31 (3H,s); 3.33 (3H,s); 3.65 (2H,m); 3.98 (1H,q,J=4 Hz); 4.18 (1H,m); 4.62 (1H,q,J=6 Hz); 5.1–5.5 (3H,m); 5.95 (1H,d,J=6 Hz); 6.0 (1H,m); 8.15 (1H,d,J=9 Hz); 8.32 (1H,s); 8.43 (1H,s); 8.6 (1H,broad s)

EXAMPLE 8

(1) In methanol (40 ml) was dissolved sodium metal (1.2 g), followed by cooling to −10° C. Then, mucochloric acid (2 g) was added gradually and the mixture was allowed to stand at 5° C. for 2 hours, followed by addition of HCl-saturated methanol (9 ml). The mixture was concentrated under reduced pressure and the residue was subjected to silica gel column chromatography using hexane-acetone (5:1) as the eluent. The active fractions were pooled and concentrated under reduced pressure to give crystals. These crystals were recrystallized from hexane to give 3,4-dihydro-3,3,5-trimethoxy-4-chloro-2(5H)-furanone as crystals (1.43 g).

m.p.: 90° C.

(2) Concentrated aqueous ammonia (10 ml) was cooled to −10° C. and 3,4-dihydro-3,3,5-trimethoxy-4-chloro-2(5H)-furanone (2 g) was gradually added. The mixture was stirred at 0° C. for about 5 minutes, at the end of which time the excess ammonia was neutralized with HCl-saturated methanol, followed by distillation under reduced pressure. The residue was extracted with chloroform, the chloroform was distilled off, and the residual oil was dissolved in methanol-HCl-saturated methanol (20 ml) and refluxed for 1 hour. The reaction mixture was concentrated under reduced pressure and the residue was subjected to silica gel column chromatography using hexane-acetone (5:3) as the eluent. The active fractions were pooled and concentrated under reduced pressure to give crystals. Recrystallization from benzene yielded 3,3,5-trimethoxy-4-chloro-2-pyrrolidinone as crystals (1.12 g).

m.p.: 141°–142° C.

(3) 3,3,5-Trimethoxy-4-chloro-2-pyrrolidinone (500 mg) was evenly admixed with adenosine 2′,3′,5′-triacetate (940 mg) and the mixture was melted and reacted at 170° C. for 1 hour. The reaction mixture was subjected to silica gel column chromatography using hexane-acetone (1:1) as the eluent to obtain $N^6$-(2-oxo-3,3-dimethoxy-4-chloro-5-pyrrolidinyl)adenosine 2′,3′,5′-triacetate (860 mg). This product was dissolved in ammonia-saturated methanol (40 ml) and allowed to stand at 5° C. for 15 hours, at the end of which time the solvent was distilled off. The residue was washed with chloroform and the insolubles were subjected to silica gel column chromatography using chloroform-methanol (10:1) as the eluent. The active fractions were pooled and concentrated under reduced pressure to give $N^6$-(2-oxo-3,3-dimethoxy-4-chloro-5-pyrrolidinyl)adenosine (590 mg).

m.p.: 110°–120° C.

u.v.; $\lambda_{max}^{C_2H_5OH}$: 265 nm (ε=19400)

IR (KBr); $\nu$max: 3600–3000 (broad), 2930, 1725, 1610 cm$^{-1}$

NMR (DMSO-d$_6$); δppm: 3.38 (3H,s); 3.40 (3H,s); 3.66 (2H,m); 4.0 (1H,m); 4.19 (1H,m); 4.7 (2H,m); 5.2–5.5 (3H,m); 5.95 (1H,d,J=6 Hz); 6.0 (1H,m); 8.3 (1H,s); 8.31 (1H,s); 8.48 (1H,s); 9.02 (1H,s)

EXAMPLE 9

Cold ammonia-saturated methanol (7 ml) was added to $N^6$-[(R)-2,5-dioxo-3-pyrrolidinyl]adenosine 2′,3′,5′-triacetate (300 mg) and the mixture was allowed to stand in a refrigerator overnight. Next morning it was concentrated under reduced pressure and the residue was subjected to high performance liquid chromatography on silica gel using chloroform-methanol-water (65:35:10) as the eluent to give a first fraction A and a second fraction B. The second fraction was concentrated under reduced pressure and the residue was freeze-dried to give $N^6$-[(R)-2,5-dioxo-3-pyrrolidinyl]adenosine as colorless powders (68.6 mg).

IR (KRr); $\nu$max: 3250, 1780, 1720, 1620 cm$^{-1}$

NMR (DMSO-d$_6$); δppm: 2.88 (2H,m); 3.64 (2H,m); 3.98 (1H,m); 4.18 (1H,q,J=4 Hz); 4.60 (1H,m), 4.9–5.6 (4H,m); 5.91 (1H,d,J=7 Hz); 8.20 (1H,s); 8.30 (1H,broad); 8.40 (1H,s); 11.20 (1H,broad)

A small amount of methanol was added to the residue obtained by the above concentration of fraction A, and the mixture was allowed to stand, whereby crystals separated out. The crystals were collected by filtration and dried to give $N^6$-[(R)-2,5-dioxo-3-pyrrolidinyl]adenosine monoacetate as colorless powders (4.78 mg).

IR (KBr); $\nu$max: 1700, 1240 cm$^{-1}$

NMR (DMSO-d$_6$) (characteristic shift), δppm: 2.0 (3H,s)

EXAMPLE 10

The following compounds were obtained in the similar manner as Example 9.

(1) N⁶-[(S)-2,5-Dioxo-3-pyrrolidinyl]adenosine
m.p.: 167°-169° C. (recrystd. from methanol)
IR (KBr); νmax: 3250, 1780, 1720, 1620 cm⁻¹
Mass spectrum: m/e=364, 261, 232, 164 135
Elemental analysis (%): Calcd. ($C_{14}H_{16}N_6O_6 \cdot \frac{1}{2}H_2O$): C, 45.04; H, 4.59; N, 22.51; Found: C, 44.83; H, 4.45; N, 22.25
NMR (DMSO-$d_6$); δppm: 2.80 (2H,m); 3.60 (2H,m); 3.95 (1H,m); 4.10 (1H,m); 4.6 (1H,m); 4.9–5.6 (4H,m); 5.86 (1H,d,J=7 Hz); 8.20 (1H,s); 8.30 (1H,broad); 8.40 (1H,s); 11.20 (1H,broad)
u.v.; $\lambda_{max}^{C_2H_5OH}$: 207, 267 nm (2) N⁶-[(S)-2,5-dioxo-3-pyrrolidinyl]adenosine monoacetate
IR (KBr); νmax: 1700, 1240 cm⁻¹
NMR (DMSO-$d_6$) (characteristic shift), δppm: 2.0 (3H,s)

EXAMPLE 11

A mixture of N⁶-[(R)-2,5-dioxo-3-pyrrolidinyl]adenosine 2′,3′,5′-triacetate (100 mg), magnesium methoxide (24 mg) and methanol (18 ml) was stirred at room temperature for 48 hours. The reaction mixture was then centrifuged (1500 r.p.m.×20 min.) to remove the precipitate formed during the reaction. The supernatant was concentrated under reduced pressure and the residue was subjected to silica gel column chromatography using ethyl acetate-methanol-water (14:2:1) as the eluent. The active fractions were pooled and concentrated under reduced pressure. The residue was dissolved in water and freeze-dried to give N⁶-[(R)-2,5-dioxo-3-pyrrolidinyl]adenosine as powders (20.2 mg).
m.p.: 167°-169° C.

EXAMPLE 12

| | |
|---|---|
| N⁶—[(R)—2,5-dioxo-3-pyrrolidinyl]adenosine | 500 g |
| Starch | 1985 g |
| Magnesium stearate | 15 g |

By the established pharmaceutical procedure, the above components were admixed and filled into 10,000 hard gelatin capsules to provide 10,000 capsules each containing 50 mg of the active component.

We claim:
1. An adenosine derivative of the general formula:

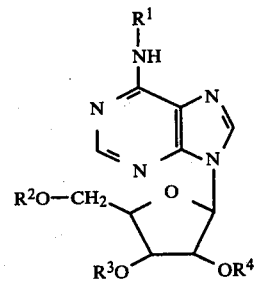

wherein
R¹ is 2,5-dioxo-3-pyrrolidinyl, and
R², R³ and R⁴ are each hydrogen or lower alkanoyl, and pharmaceutically acceptable salts thereof.
2. A compound according to claim 1, wherein R¹ is (R)-2,5-dioxo-3-pyrrolidinyl.
3. A compound according to claim 2, which is N⁶-[(R)-2,5-dioxo-3-pyrrolidinyl]adenosine.
4. An anti-hypertension pharmaceutical composition containing an anti-hypertensive effective amount of one or more adenosine derivatives of the general formula:

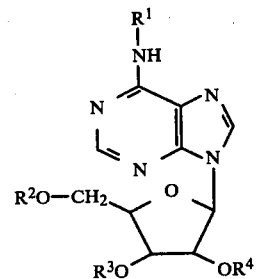

wherein
R¹ is 2,5-dioxo-3-pyrrolidinyl, and
R², R³ and R⁴ are each hydrogen or lower alkanoyl, and pharmaceutically acceptable salts thereof, in admixture with pharmaceutically acceptable carriers.

* * * * *